US005976865A

United States Patent [19]

Lal et al.

[11] Patent Number: 5,976,865

[45] Date of Patent: Nov. 2, 1999

[54] VESICLE TRANSPORT RELATED PROTEIN

[75] Inventors: Preeti Lal, Santa Clara; Neil C. Corley, Mountain View; Purvi Shah, Sunnyvale, all of Calif.

[73] Assignee: Incyte Pharmaceuticals, Inc., Palo Alto, Calif.

[21] Appl. No.: 08/984,172

[22] Filed: Dec. 3, 1997

[51] Int. Cl.[6] .............................. C12N 15/11; C12N 1/21; C12N 15/63; C12Q 1/68

[52] U.S. Cl. ...................................... 435/252.3; 435/320.1; 435/254.3; 435/325; 435/69.1; 435/6; 435/91; 514/44; 536/23.1; 536/23.5

[58] Field of Search ................................ 536/23.1, 24.31, 536/23.5; 435/69.1, 320.1, 252.3, 254.2, 325, 6, 91; 514/44

[56] References Cited

FOREIGN PATENT DOCUMENTS 9514772 6/1995 WIPO .

OTHER PUBLICATIONS

Rothman, J.E. and F.T. Wieland, "Protein Sorting by Transport Vesicles", *Science*, 272:227–234 (1996).

Görlich, D. et al., "A Mammalian Homolog of SEC61p and SECYp Is Associated with Ribosomes and Nascent Polypeptides during Translocation", *Cell*, 71:489–503 (1992).

Blobel, G. and B. Dobberstein, "Transfer of Proteins Across Membranes II. Resconstitution of Functional Rough Microsomes from Heterologous Components.", *J. Cell Biol.*, 67:852–862 (1975).

Birkenmeier, C.S. et al., "Complex Patterns of Sequence Variation and Multiple 5' and 3' Ends Are Found among Transcripts of the Erythroid Ankyrin Gene", *J. Biol. Chem.*, 268:9533–9540 (1993).

Lambert, S. et al., "cDNA sequence for human erythrocyte ankyrin", *Proc. Natl. Acad. Sci.USA*, 87:1730–1734 (1990).

Coetzer, T.L. et al., "Partial Ankyrin and Spectrin Deficiency in Severe, Atypical Hereditary Spherocytosis", *N. Engl. J. Med.*, 318:230–234 (1988).

Birkermeier, C.S. et al, (Direct Submission), GenBank Sequence Database (Accession U73972), National Center for Biotechnology Information, National Library of Medicine, Bethesda, Maryland, 20894 (GI 1658115; GI 1658116), Nov. 5, 1996.

Hall, T.G. and V. Bennett, "Regulatory Domains of Erythrocyte Ankyrin", *J. Biol. Chem.*, 262:10537–10545 (1987).

Blumenthal, K.M. and W.R. Kem, (Direct Submission), GenBank Sequence Database (Accession 118064), National Center for Biotechnology Information, National Library of Medicine, Bethesda, Maryland, 20894 (GI 118064), Feb. 1, 1995.

"Biochemistry", Lehninger 1975 p. 962 Worth Publishers, New York, NY.

Promega 1994–1995 p. 167.

New England Biolabs 1993–1994 pp. 152–153.

Lambert, PNAS 87:1730, 1990.

*Primary Examiner*—Nancy A. Johnson
*Attorney, Agent, or Firm*—Incyte Pharmaceuticals, Inc.

[57] ABSTRACT

The invention provides a human vesicle transport related protein (VTRP) and polynucleotides which identify and encode VTRP. The invention also provides expression vectors, host cells, antibodies, agonists, and antagonists. The invention also provides methods for treating or preventing disorders associated with expression of VTRP.

10 Claims, 7 Drawing Sheets

```
                9              18              27              36              45              54
5' NNG CCG AGA GGG CCA TTC GGT GTC CTG CCC ACA GAG AGA GAA ACA GTG AGA GAC

               63              72              81              90              99             108
   CAA GAG AGC AAA CCA GAG AGA TAC GGA GGG GGA ATG CAA GGG GTC CCT GGG GGA

              117             126             135             144             153             162
   CTC AGG AGT CCC AGT GGA GAA TGA GAG GCA GGC CCC CCG TGG TGG CCG GGG CCC

              171             180             189             198             207             216
   TGG CTG CCA GAG GAC CGG GCT GGT GAG GAG GCG AGG ATG TGG ACT TTC GTC ACC
                                                    M   W   T   F   V   T

              225             234             243             252             261             270
   CAG CTG TTG GTC ACG CTG GTG CTG CTG AGC TTC TTC CTG GTC AGC TGT CAG AAC
   Q   L   L   V   T   L   V   L   L   S   F   F   L   V   S   C   Q   N

              279             288             297             306             315             324
   GTG ATG CAC ATT GTC AGG GGG TCC CTG TGC TTT GTG CTA AAG CAC ATC CAC CAG
   V   M   H   I   V   R   G   S   L   C   F   V   L   K   H   I   H   Q

           333             342             351             360             369             378
   GAG CTG GAC AAG GAG CTG GGG GAG AGC GAG GGC CTC AGT GAC GAC GAG GAG ACC
   E   L   D   K   E   L   G   E   S   E   G   L   S   D   D   E   E   T
```

FIGURE1A

```
                387                 396                 405                 414                 423                 432
ATC TCC ACC AGG GTG GTC CGG CGG CGG GTC TTC CTG AAG GGG AAT GAG TTT CAG
I   S   T   R   V   V   R   R   R   V   F   L   K   G   N   E   F   Q

                441                 450                 459                 468                 477                 486
AAT ATT CCA GGG GAG CAG GTG ACA GAG GAG CAA TTC ACG GAT GAG CAG GGC AAC
N   I   P   G   E   Q   V   T   E   E   Q   F   T   D   E   Q   G   N

                495                 504                 513                 522                 531                 540
ATT GTC ACC AAG AAG ATC ATT CGC AAG GTG GTT CGA CAG ATA GAC TTG TCC AGC
I   V   T   K   K   I   I   R   K   V   V   R   Q   I   D   L   S   S

                549                 558                 567                 576                 585                 594
GCC GAT GCC GCC CAG GAG CAC GAG GAG GTG GAG CTG AGA GGG AGT GCC CTA CAG
A   D   A   A   Q   E   H   E   E   V   E   L   R   G   S   A   L   Q

                603                 612                 621                 630                 639                 648
CCG GAC CTG ATA GAG GCC AGG AAG GGG GCG CAG ATA TTG AAG CGG GCC AGC CTG
P   D   L   I   E   A   R   K   G   A   Q   I   L   K   R   A   S   L

                657                 666                 675                 684                 693                 702
AAA AAG GGG GAA ACA GTG ACC CCG AGC CGC TCT CCT TGG AGT AGC CTC TCG GGA
K   K   G   E   T   V   T   P   S   R   S   P   W   S   S   L   S   G

                711                 720                 729                 738                 747                 756
GGA TCA CAC CTC GAC ACC CAA CCC CTG AAC CCC ACA CAC TCT GCC ATG CAC ACA
G   S   H   L   D   T   Q   P   L   N   P   T   H   S   A   M   H   T
```

FIGURE 1B

```
              765             774             783             792             801             810
GGA GGA GAG CTG GAC CTG AGG GCC ACC GCA GCG GTG CAC ACA TTC CTC TGG GCT
G   G   E   L   D   L   R   A   T   A   A   V   H   T   F   L   W   A

              819             828             837             846             855             864
GAC GGC ATG ACC TCT GTA AGG GAC TCC TGC TAG TCC CCT CTT GGC ATG AAT GAC
D   G   M   T   S   V   R   D   S   C

              873             882             891             900             909             918
TGA CTG TAG ACG CAT GAC CTC CAG GCT TCA ATC CTG CCT CTT GCA ATG ACA GCT

              927             936             945             954             963             972
GAT CTG TCG GAA CCA GGA CAC AAA AGC AGC AAG AAG CGG GGA GAG AGA GGG ATA

              981             990             999            1008            1017            1026
GAA AAC AAG CGC AGG AGA GCC TGC GAA CGC AAA AGT GAA TGA GGG CTT TTT GTG

             1035            1044            1053            1062            1071            1080
GCT GGG GAT GGG TTT TGG TTT TGG GGT TTT TTT TTT TTA AAT TGT TTT GAC TCC
```

FIGURE 1C

Figure 1D:
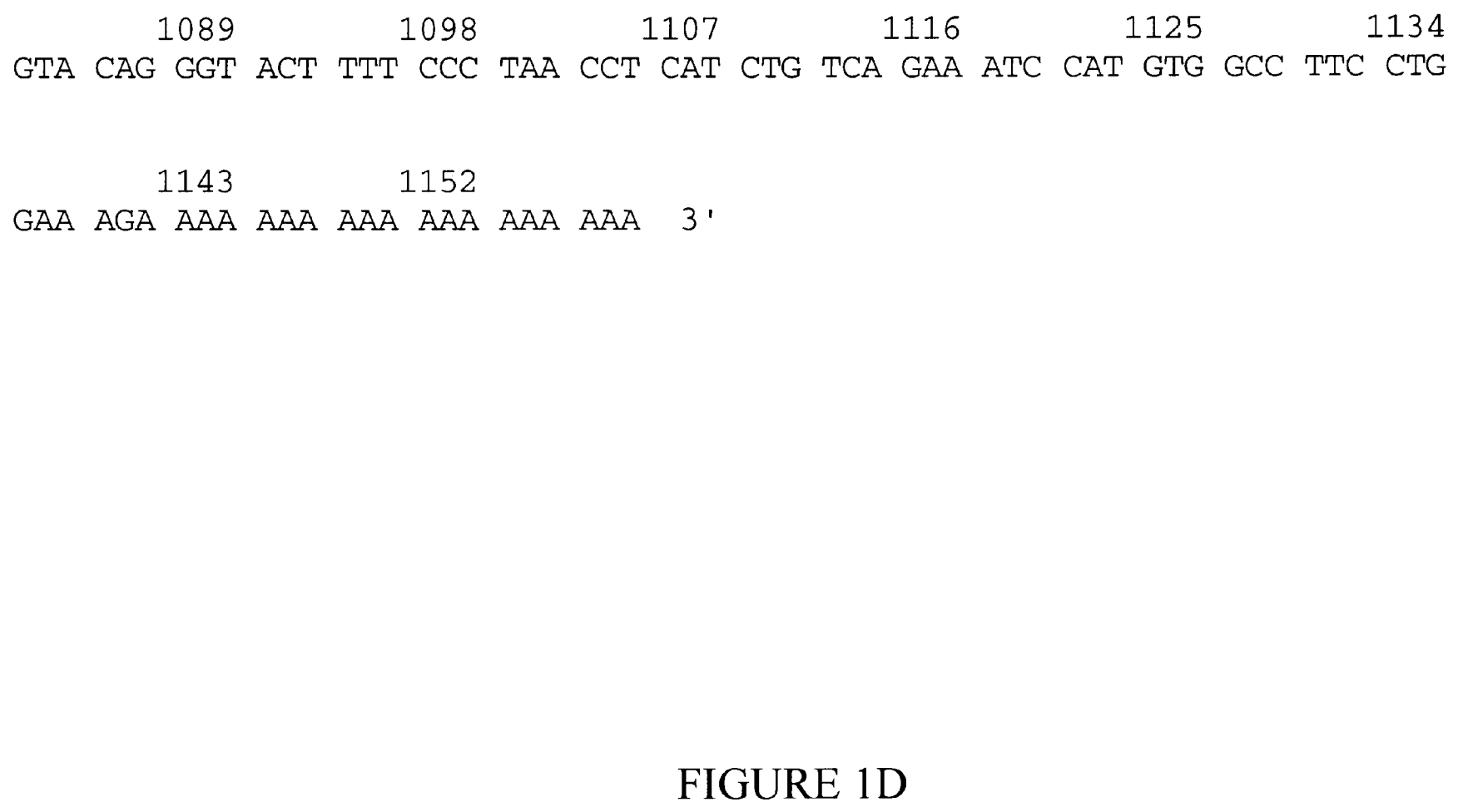

```
        1089          1098          1107          1116          1125          1134
GTA CAG GGT ACT TTT CCC TAA CCT CAT CTG TCA GAA ATC CAT GTG GCC TTC CTG

        1143          1152
GAA AGA AAA AAA AAA AAA AAA AAA  3'
```

```
1   M W T F V T Q L L V T L V L L S F F L V S C Q N V M H I V R G S L C F V L K H I  g118064
1   M W T F I T Q L L V T L V L L G F F L V S C Q N V M H I V K G S L C F V L K H I  g1658115

41  H Q E L D K E L G E S E G L S D D E E T I S T R V V R R R V F L K G N E F Q N I  g118064
41  H Q E L D K E L G E S E G L S D D E E T I S T R V V R R R V F L K G D E L Q N I  g1658115

81  P G E Q V T E E Q F T D E Q G N I V T K K I I R K V V R Q I D L S S A D A A Q E  g118064
81  P G E Q V T E E Q F T D E Q G N I V T K K I I R K V V R Q V D S S G A I D T Q Q  g1658115

121 H E E V E L R G S A L Q P D L I E A R K G A Q I L K R A S L K K G E T V T P S R  g118064
121 H E E V E L R G S G L Q P D L I E G R K G A Q I V K R A S L K R G K Q            g1658115

161 S P W S S L S G G S H L D T Q P L N P T H S A M H T G G E L D L R A T A A V H T  g118064
155                                                                                  g1658115

201 F L W A D G M T S V R D S C                                                      g118064
155                                                                                  g1658115
```

VESICLE TRANSPORT RELATED PROTEIN

FIELD OF THE INVENTION

This invention relates to nucleic acid and amino acid sequences of a vesicle transport related protein and to the use of these sequences in the diagnosis, treatment, and prevention of cancer and immune disorders.

BACKGROUND OF THE INVENTION

Vesicle transport is the general process in eukaryotic cells by which proteins synthesized in the endoplasmic reticulum (ER) are transported via the Golgi network to the various compartments in the cell where they will function. Other proteins are transported to the cell surface by this process where they may be secreted. Such proteins include membrane bound receptors or other membrane proteins, neurotransmitters, hormones, and digestive enzymes. The transport process uses a series of transport vesicles that shuttle a protein from one membrane-bound compartment (donor compartment) to another (acceptor compartment) until the protein reaches its proper destination (Rothman, J. E and F. T Wieland (1996) Science 272:227–34).

Protein transport across the ER involves a process that is similar in bacteria, yeast and mammals (Gorlich, D. et al. (1992) Cell 71: 489–503). In the mammalian system, transport is initiated by the action of a cytoplasmic signal recognition particle (SRP) which recognizes a signal sequence on a growing, nascent polypeptide and binds the polypeptide and its ribosome complex to the ER membrane through an SRP receptor located on the membrane. The signal peptide is cleaved and the ribosome complex, together with the attached polypeptide, becomes membrane bound. The mechanism of the subsequent protein translocation process across the ER membrane is largely unknown. It is believed to involve the transient formation of a protein-conducting channel by transmembrane proteins interacting with one another and with the membrane-bound ribosome (Blobel, G. and B. Dobberstein (1975) J. Cell Biol. 67: 852–62).

Possible proteins involved in the ER translocation process in yeast include SEC61p, SEC62p, and SEC63p. Mutations in the genes encoding these proteins lead to defects in the translocation process. SEC61 may be of particular importance since certain mutations in the gene for this protein inhibit the translocation of all proteins tested (Gorlich et al., supra).

Mammalian homologs of yeast SEC61 (mSEC61) have been identified in dog and rat (Gorlich et al., supra). Mammalian SEC61 is also structurally similar to the bacterial cytoplasmic membrane, translocation protein, SECYp. mSEC61 is found in tight association with membrane-bound ribosomes, an association that is induced by membrane-targeting of nascent polypeptide chains and is weakened by dissociation of the ribosomes into their subunits. These studies indicate that mSEC61 is a component of a postulated protein-conducting channel in the ER membrane, and that nascent polypeptides are transferred from the ribosome to this channel (Gorlich et al., supra).

Another aspect of the protein/vesicle transport process, are interactions that occur at the cell membrane control the transport of proteins out of or into a cell. Key to this part of the process are interactions between the cell membrane and a supporting membrane cytoskeleton based on the protein spectrin. A large family of related proteins called ankyrins participate in this part of the transport process by binding to the membrane skeleton protein spectrin and to a protein in the cell membrane called band 3, a component of the anion channel in the cell membrane. Ankyrins therefore function as a critical link between the cytoskeleton and the cell membrane.

Originally found in association with erythroid cells, ankyrins are also found in other tissues as well (Birkenmeier, C. S. et al. (1993) J. Biol. Chem. 268: 9533–40). Ankyrins are large proteins (~1800 amino acids) containing an N-terminal, 89 kDa domain that binds the cell membrane proteins band 3 and tubulin, a central 62 kDa domain that binds the cytoskeletal proteins spectrin and vimenetin, and a C-terminal, 55 kDa regulatory domain that functions as a modifier of the binding activities of the other two domains. Individual genes for ankyrin are able to produce multiple ankyrin isoforms by various insertions and deletions. These isoforms are of nearly identical size but may have different functions. In addition, smaller transcripts are produced which are missing large regions of the coding sequences from the N-terminal (band 3 binding), and central (spectrin binding) domains. The existence of such a large family of ankyrin proteins and the observation that more than one type of ankyrin may be expressed in the same cell type suggests that ankyrins may have more specialized functions than simply binding the membrane skeleton to the plasma membrane (Birkenmeier et al., supra).

In humans, two isoforms of ankyrin are expressed, alternatively, in developing erythroids and mature erythroids, respectively (Lambert, S. et. al. (1990) Proc. Natl. Acad. Sci. 87: 1730–34). A deficiency in erythroid spectrin and ankyrin has been associated with the hemolytic anemia, hereditary spherocytosis (Coetzer, T. L., et al. (1988) N. Engl. J. Med. 318: 230–34).

The discovery of new vesicle transport related proteins and the polynucleotides encoding these proteins satisfies a need in the art by providing new compositions which are useful in the diagnosis, treatment, and prevention of cancer and immune disorders.

SUMMARY OF THE INVENTION

The invention features a substantially purified polypeptide, vesicle transport related protein (VTRP), comprising the amino acid sequence of SEQ ID NO:1 or a fragment of SEQ ID NO:1.

The invention further provides a substantially purified variant of VTRP having at least 90% amino acid identity to the amino acid sequence of SEQ ID NO:1 or a fragment of SEQ ID NO:1. The invention also provides an isolated and purified polynucleotide sequence encoding the polypeptide comprising the amino acid sequence of SEQ ID NO:1 or a fragment of SEQ ID NO:1. The invention also includes an isolated and purified polynucleotide variant having at least 90% polynucleotide identity to the polynucleotide sequence encoding the polypeptide comprising the amino acid sequence of SEQ ID NO:1 or a fragment of SEQ ID NO:1.

Additionally, the invention provides a composition comprising a polynucleotide sequence encoding the polypeptide comprising the amino acid sequence of SEQ ID NO:1 or a fragment of SEQ ID NO:1. The invention further provides an isolated and purified polynucleotide sequence which hybridizes under stringent conditions to the polynucleotide sequence encoding the polypeptide comprising the amino acid sequence of SEQ ID NO:1 or a fragment of SEQ ID NO:1, as well as an isolated and purified polynucleotide sequence which is complementary to the polynucleotide sequence encoding the polypeptide comprising the amino acid sequence of SEQ ID NO:1 or a fragment of SEQ ID NO:1.

The invention also provides an isolated and purified polynucleotide sequence comprising SEQ ID NO:2 or a fragment of SEQ ID NO:2, and an isolated and purified polynucleotide variant having at least 90% polynucleotide identity to the polynucleotide sequence comprising SEQ ID NO:2 or a fragment of SEQ ID NO:2. The invention also provides an isolated and purified polynucleotide sequence which is complementary to the polynucleotide sequence comprising SEQ ID NO:2 or a fragment of SEQ ID NO:2.

The invention further provides an expression vector containing at least a fragment of the polynucleotide sequence encoding the polypeptide comprising the amino acid sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide sequence encoding VTRP under conditions suitable for the expression of the polypeptide; and (b) recovering the polypeptide from the host cell culture.

The invention also provides a pharmaceutical composition comprising a substantially purified VTRP having the amino acid sequence of SEQ ID NO:1 or a fragment of SEQ ID NO:1 in conjunction with a suitable pharmaceutical carrier.

The invention further includes a purified antibody which binds to a polypeptide comprising the amino acid sequence of SEQ ID NO:1 or a fragment of SEQ ID NO:1, as well as a purified agonist and a purified antagonist of the polypeptide.

The invention also provides a method for treating or preventing a cancer, the method comprising administering to a subject in need of such treatment an effective amount of an antagonist of VTRP.

The invention also provides a method for treating or preventing an immune disorder, the method comprising administering to a subject in need of such treatment an effective amount of an antagonist of VTRP.

The invention also provides a method for detecting a polynucleotide encoding VTRP in a biological sample containing nucleic acids, the method comprising the steps of: (a) hybridizing the complement of the polynucleotide sequence encoding the polypeptide comprising SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding VTRP in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of VTRP. The alignment was produced using MACDNASIS PRO software (Hitachi Software Engineering Co. Ltd., San Bruno, Calif.).

FIG. 2 shows the amino acid sequence alignments between VTRP (118064; SEQ ID NO:1) and mouse erythroid ankyrin, ANK1 (GI 1658116; SEQ ID NO:3), produced using the multisequence alignment program of DNASTAR software (DNASTAR Inc, Madison Wis.).

DESCRIPTION OF THE INVENTION

Figure 3A:
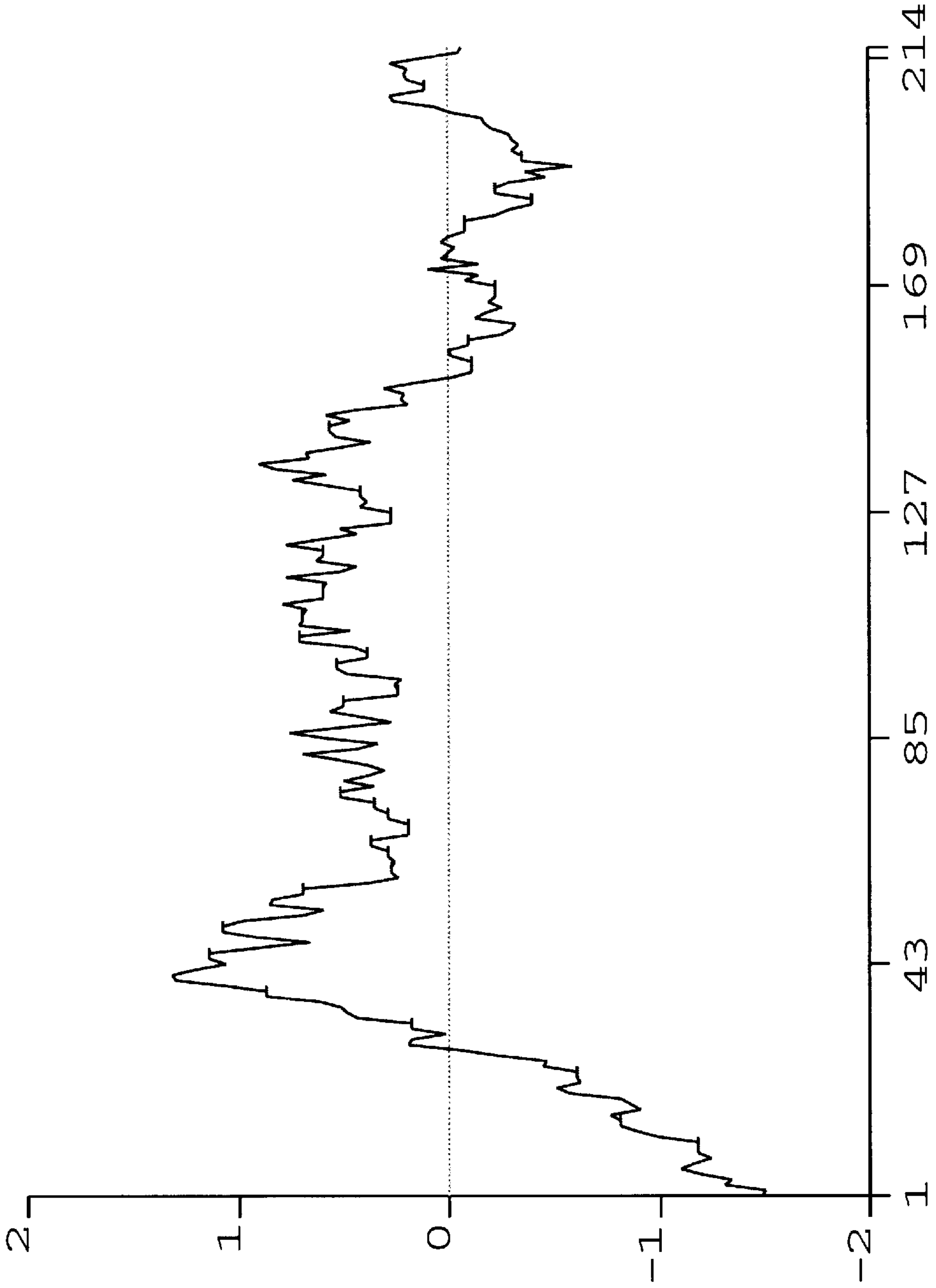
FIGS. 3A and 3B show the hydrophobicity plots for VTRP (SEQ ID NO:1) and mouse ANK1 (SEQ ID NO:3), respectively; the positive X axis reflects amino acid position and the negative Y axis reflects hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"VTRP," as used herein, refers to the amino acid sequences of substantially purified VTRP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to VTRP, increases or prolongs the duration of the effect of VTRP. Agonists may include proteins, nucleic acids, carbohydrates, or any other molecules which bind to and modulate the effect of VTRP.

An "allele" or an "allelic sequence," as these terms are used herein, is an alternative form of the gene encoding VTRP. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding VTRP, as described herein, include those sequences with deletions, insertions, or substitutions of different nucleotides, resulting in a polynucleotide the same VTRP or a polypeptide with at least one functional characteristic of VTRP. Included within this definition are polymorphisms which may or may not be readily detectable using a particular oligonucleotide probe of the polynucleotide encoding VTRP, and improper or unexpected hybridization to alleles, with a locus other than the normal chromosomal locus for the polynucleotide sequence encoding VTRP. The encoded protein may also be "altered," and may contain deletions, insertions, or substitutions of amino acid residues which produce a silent change and result in a functionally equivalent VTRP. Deliberate amino acid substitutions may be made on the basis of similarity in polarity, charge, solubility, hydrophobicity, hydrophilicity, and/or the amphipathic nature of the residues, as long as the biological or immunological activity of VTRP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments" refers to fragments of VTRP which are preferably about 5 to about 15 amino acids in length and which retain some biological activity or immunological activity of VTRP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, for example, Dieffenbach, C. W. and G. S. Dveksler (1995) *PCR Primer, a Laboratory Manual*, Cold Spring Harbor Press, Plainview, N.Y.)

The term "antagonist," as it is used herein, refers to a molecule which, when bound to VTRP, decreases the amount or the duration of the effect of the biological or immunological activity of VTRP. Antagonists may include proteins, nucleic acids, carbohydrates, antibodies, or any other molecules which decrease the effect of VTRP.

As used herein, the term "antibody" refers to intact molecules as well as to fragments thereof, such as Fab, $F(ab')_2$, and Fv fragments, which are capable of binding the epitopic determinant. Antibodies that bind VTRP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific DNA or RNA sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic VTRP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding VTRP or fragments of VTRP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR Kit (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding VTRP, by northern analysis is indicative of the presence of nucleic acids encoding VTRP in a sample, and thereby correlates with expression of the transcript from the polynucleotide encoding VTRP.

A "deletion," as the term is used herein, refers to a change in the amino acid or nucleotide sequence that results in the absence of one or more amino acid residues or nucleotides.

The term "derivative," as used herein, refers to the chemical modification of VTRP, of a polynucleotide sequence encoding VTRP, or of a polynucleotide sequence complementary to a polynucleotide sequence encoding VTRP. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains a at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

"Human artificial chromosomes" (HACs), as described herein, are linear microchromosomes which may contain DNA sequences of about 10 K to 10 M in size, and which contain all of the elements required for stable mitotic chromosome segregation and maintenance. (Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of VTRP. For example, modulation may cause an increase or a decrease in protein activity, binding characteristics, or any other biological, functional, or immunological properties of VTRP.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (Nielsen, P. E. et al. (1993) Anticancer Drug Des. 8:53–63.

The term "sample," as used herein, is used in its broadest sense. A biological sample suspected of containing nucleic acids encoding VTRP, or fragments thereof, or VTRP itself may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences.

Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% fornamide, 5X SSPE, 0.3% SDS, and 200 µg/ml sheared and denatured salmon sperm DNA. Hybridization could occur under reduced stringency conditions as described above, but in 35% formnamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformations selected based on the type of host cell being transformed and may include, but is not limited to, viral infection, electroporation, heat shock, lipofection, and particle bombardment. The term "transformned" cells includes stably transformed cells in which the inserted DNA is capable of replication either as an autonomously replicating plasmid or as part of the host chromosome, and refers to cells which transiently express the inserted DNA or RNA for limited periods of time.

A "variant" of VTRP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human vesicle transport related protein (VTRP), the polynucleotides encoding VTRP, and the use of these compositions for the diagnosis, treatment, or prevention of cancer and immune disorders.

Nucleic acids encoding the VTRP of the present invention were first identified in Incyte Clone 118064 from the skeletal muscle cDNA library (MUSCNOT01) using a computer search for amino acid sequence alignments. A consensus sequence, SEQ ID NO:2, was derived from the following overlapping and/or extended nucleic acid sequences: Incyte Clones 118064 (MUSCNOT01), 2234090, (PANCTUTO2), 2638847 (BONTNOT01), and 945479 (RATRNOT02).

Figure 3B:
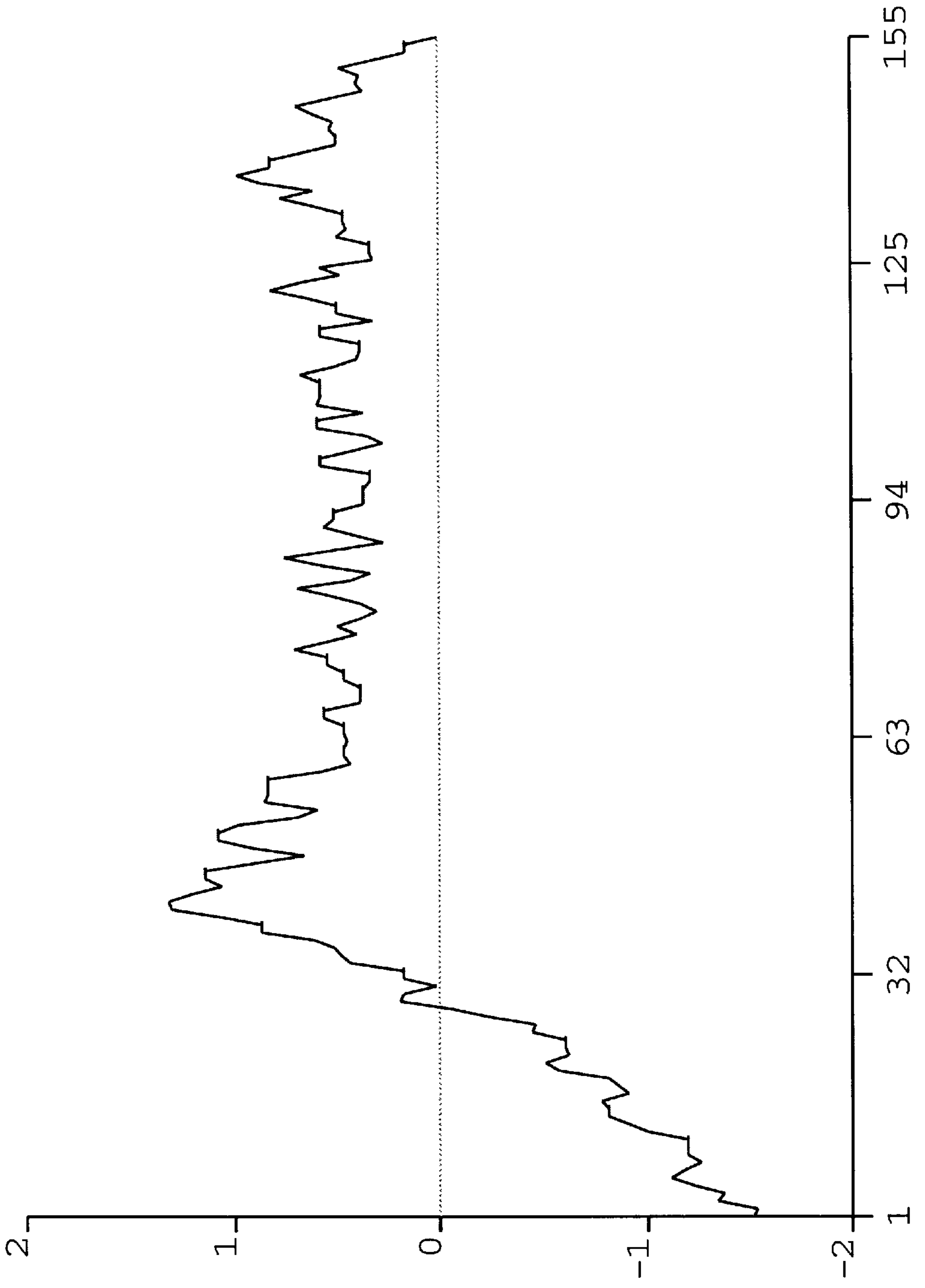

In one embodiment, the invention encompasses a polypeptide comprising the amino acid sequence of SEQ ID NO:1 as shown in FIGS. 1A, 1B, 1C, and 1D. VTRP is 214 amino acids in length and has several potential protein phosphorylation sites for cAMP/cGMP-dependent protein kinase at residue S149, for casein kinase II at residues S55, S113, S170, T186, and S209, and for protein kinase C at residues S62, T99, S149, and S209. As shown in FIG. 2, VTRP-1 has chemical and structural homology with mouse erythroid ANK1 (GI 1658116; SEQ ID NO:3). In particular, VTRP and mouse ANK1 share 88% identity. Mouse ANK1 shares many of the potential protein kinase phosphorylation sites found in VTRP. VTRP is distinguished from mouse ANK1 and other ankyrin proteins found in the GenBank databases by a unique C-terminal sequence beginning at approximately residue E154 and extending to the end of the molecule. As illustrated by FIGS. 3A and 3B, VTRP and mouse ANK1 have rather similar hydrophobicity plots. In particular, a notable region of hydrophobicity is apparent in the N-terminal region of both proteins extending from approximately residues 1 to 30. Northern analysis shows the expression of this sequence in various libraries, at least 50% of which are immortalized or cancerous.

The invention also encompasses VTRP variants. A preferred VTRP variant is one having at least about 80%, more preferably at least about 90%, and most preferably at least about 95% amino acid sequence identity to the VTRP amino acid sequence.

The invention also encompasses polynucleotides which encode VTRP. In a particular embodiment, the invention encompasses a polynucleotide sequence comprising the sequence of SEQ ID NO:2, as shown in FIGS. 1A, 1B, 1C, and 1D.

The invention also encompasses a variant of a polynucleotide sequence encoding VTRP. In particular, such a variant polynucleotide sequence will have at least about 80%, more preferably at least about 90%, and most preferably at least about 95% polynucleotide sequence identity to the polynucleotide sequence encoding VTRP. A particular aspect of the invention encompasses a variant of SEQ ID NO:2 which has at least about 80%, more preferably at least about 90%, and most preferably at least about 95% polynucleotide sequence identity to SEQ ID NO:2.

It will be appreciated by those skilled in the art that as a result of the degeneracy of the genetic code, a multitude of polynucleotide sequences encoding VTRP, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring VTRP, and all such variations are to be considered as being specifically disclosed.

Although nucleotide sequences which encode VTRP and its variants are preferably capable of hybridizing to the nucleotide sequence of the naturally occurring VTRP under appropriately selected conditions of stringency, it may be advantageous to produce nucleotide sequences encoding VTRP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding VTRP and its derivatives without altering the encoded amino acid sequences include the production of RNA transcripts having more desirable properties, such as a greater half-life, than transcripts produced from the naturally occurring sequence.

The invention also encompasses production of DNA sequences which encode VTRP and VTRP derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding VTRP or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing are well known and generally available in the art and may be used to practice any of the embodiments of the invention. The methods may employ such enzymes as the Klenow fragment of DNA polymerase I, SEQUENASE DNA polymerase (U.S. Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (GIBCO/BRL, Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.) and the ABI CATALYST and 373 and 377 DNA sequencers (Perkin Elmer).

The nucleic acid sequences encoding VTRP may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (Sarkar, G. (1993) PCR Methods Applic. 2:318–322.) In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (Triglia, T. et al. (1988) Nucleic Acids Res. 16:8186.) The primers may be designed using commercially available software such as OLIGO 4.06 Primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR software, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode VTRP may be used in recombinant DNA molecules to direct expression of VTRP, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express VTRP.

As will be understood by those of skill in the art, it may be advantageous to produce VTRP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter VTRP encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding VTRP may be ligated to a heterologous sequence to encode a fusion protein. For example, to screen peptide libraries for inhibitors of VTRP activity, it may be useful to encode a chimeric VTRP protein that can be recognized by a commercially available antibody. A fusion protein may also be engineered to contain a cleavage site located between the VTRP encoding sequence and the heterologous protein sequence, so that VTRP may be cleaved and purified away from the heterologous moiety.

In another embodiment, sequences encoding VTRP may be synthesized, in whole or in part, using chemical methods well known in the art. (See Caruthers, M. H. et al. (1980) Nucl. Acids Res. Symp. Ser. 7:215–223, and Horn, T. et al. (1980) Nucl. Acids Res. Symp. Ser. 7:225–232.) Alternatively, the protein itself may be produced using chemical methods to synthesize the amino acid sequence of VTRP, or a fragment thereof. For example, peptide synthesis can be performed using various solid-phase techniques (Roberge, J. Y. et al. (1995) Science 269:202–204) and automated synthesis may be achieved using the ABI 431A peptide synthesizer (Perkin Elmer).

The newly synthesized peptide may be substantially purified by preparative high performance liquid chromatography. (See, for example, Creighton, T. (1983) *Proteins, Structures and Molecular Principles*, WH Freeman and Co., New York, N.Y.) The composition of the synthetic peptides may be confirmed by amino acid analysis or by sequencing. (See, for example, the Edman degradation procedure described in Creighton, supra.) Additionally, the amino acid sequence of VTRP, or any part thereof, may be altered during direct synthesis and/or combined with sequences from other proteins, or any part thereof, to produce a variant polypeptide.

In order to express a biologically active VTRP, the nucleotide sequences encoding VTRP or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding VTRP and appropriate transcriptional and translational control elements. These methods include in vitro recombinant DNA techniques, synthetic techniques, and in vivo genetic recombination. Such techniques are described in Sambrook, J. et al. (1989*; Molecular Cloning, A Laboratory Manual*, Cold Spring Harbor Press, Plainview, N.Y.) and Ausubel, F. M. et al. (1989*; Current Protocols in Molecular Biology*, John Wiley & Sons, New York, N.Y.).

A variety of expression vector/host systems may be utilized to contain and express sequences encoding VTRP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding VTRP, vectors based on SV40 or EBV may be used with an appropriate selectable marker.

In bacterial systems, a number of expression vectors may be selected depending upon the use intended for VTRP. For example, when large quantities of VTRP are needed for the induction of antibodies, vectors which direct high level expression of fusion proteins that are readily purified may be used. Such vectors include, but are not limited to, multifunctional *E. coli* cloning and expression vectors such as the BLUESCRIPT phagemid (Stratagene), in which the sequence encoding VTRP may be ligated into the vector in frame with sequences for the amino-terminal Met and the subsequent 7 residues of β-galactosidase so that a hybrid protein is produced, pIN vectors (Van Heeke, G. and S. M. Schuster (1989) J. Biol. Chem. 264:5503–5509), and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. For reviews, see Ausubel (supra) and Grant et al. (1987; Methods Enzymol. 153:516–544).

In cases where plant expression vectors are used, the expression of sequences encoding VTRP may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, for example, Hobbs, S. or Murry, L. E. in *McGraw Hill Yearbook of Science and Technology* (1992) McGraw Hill, New York, N.Y.; pp. 191–196.)

An insect system may also be used to express VTRP. For example, in one such system, *Autographa californica* nuclear polyhedrosis virus (AcNPV) is used as a vector to express foreign genes in *Spodoptera frugiperda* cells or in *Trichoplusia larvae*. The sequences encoding VTRP may be cloned into a non-essential region of the virus, such as the polyhedrin gene, and placed under control of the polyhedrin promoter. Successful insertion of VTRP will render the polyhedrin gene inactive and produce recombinant virus lacking coat protein. The recombinant viruses may then be used to infect, for example, *S. frugiperda* cells or *Trichoplusia larvae* in which VTRP may be expressed. (Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding VTRP may be ligated into an adenovirus transcription/translation complex consisting of the late promoter and tripartite leader sequence. Insertion in a non-essential E1 or E3 region of the viral genome may be used to obtain a viable virus which is capable of expressing VTRP in infected host cells. (Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 M to 10 M are constructed and delivered via conventional delivery methods (liposomes, polycationic amino polymers, or vesicles) for therapeutic purposes.

Specific initiation signals may also be used to achieve more efficient translation of sequences encoding VTRP. Such signals include the ATG initiation codon and adjacent sequences. In cases where sequences encoding VTRP and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing VTRP can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223–32) and adenine phosphoribosyltransferase genes (Lowy, I. et al. (1980) Cell 22:817–23), which can be employed in $tk^-$ or $apr^-$ cells, respectively. Also, antimetabolite, antibiotic, or herbicide resistance can be used as the basis for selection. For example, dhft confers resistance to methotrexate (Wigler, M. et al. (1980) Proc. Natl. Acad. Sci. 77:3567–70); npt confers resistance to the aminoglycosides neomycin and G-418 (Colbere-Garapin, F. et al (1981) J. Mol. Biol. 150:1–14); and als or pat confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047–51.) Recently, the use of visible markers has gained popularity with such markers as anthocyanins, B glucuronidase and its substrate GUS, and luciferase and its substrate luciferin. These markers can be used not only to identify transformants, but also to quantify the amount of transient or stable protein expression attributable to a specific vector system. (Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding VTRP is inserted within a marker gene sequence, transformed cells containing sequences encoding VTRP can be identified by the absence of marker gene function. Alternatively, a marker gene can be placed in tandem with a sequence encoding VTRP under the control of a single promoter. Expression of the marker gene in response to induction or selection usually indicates expression of the tandem gene as well.

Alternatively, host cells which contain the nucleic acid sequence encoding VTRP and express VTRP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding VTRP can be detected by DNA-DNA or DNA-RNA hybridization or amplification using probes or fragments or fragments of polynucleotides encoding VTRP. Nucleic acid amplification based assays involve the use of oligonucleotides or oligomers based on the sequences encoding VTRP to detect transformants containing DNA or RNA encoding VTRP.

A variety of protocols for detecting and measuring the expression of VTRP, using either polyclonal or monoclonal antibodies specific for the protein, are known in the art. Examples of such techniques include enzyme-linked immnunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on VTRP is preferred, but a competitive binding assay may be employed. These and other assays are well described in the art, for example, in Hampton, R. et al. (1990*; Serological Methods, a Laboratory Manual*, APS Press, St Paul, Minn.) and in Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding VTRP include oligolabeling, nick translation, end-labeling, or PCR amplification using a labeled nucleotide. Alternatively, the sequences encoding VTRP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding VTRP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode VTRP may be designed to contain signal sequences which direct secretion of VTRP through a prokaryotic or eukaryotic cell membrane. Other constructions may be used to join sequences encoding VTRP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized inmmunoglobulin, and the domain utilized in the FLAG extension/affinity purification system (Immunex Corp., Seattle, Wash.). The inclusion of cleavable linker sequences, such as those specific for Factor XA or enterokinase (Invitrogen, San Diego, Calif.), between the purification domain and the VTRP encoding sequence may be used to facilitate purification. One such expression vector provides for expression of a fusion protein containing VTRP and a nucleic acid encoding 6 histidine residues preceding a thioredoxin or an enterokinase cleavage site. The histidine residues facilitate purification on immobilized metal ion affinity chromatography (IMIAC; described in Porath, J. et al. (1992) Prot. Exp. Purif. 3: 263–281)), while the enterokinase cleavage site provides a means for purifying VTRP from the fusion protein. A discussion of vectors which contain fusion proteins is provided in Kroll, D. J. et al. (1993; DNA Cell Biol. 12:441–453).

Fragments of VTRP may be produced not only by recombinant production, but also by direct peptide synthesis using solid-phase techniques. (Merrifield J. (1963) J. Am. Chem. Soc. 85:2149–2154.) Protein synthesis may be performed by manual techniques or by automation. Automated synthesis may be achieved, for example, using the Applied Biosystems 431A peptide synthesizer (Perkin Elmer). Various fragments of VTRP may be synthesized separately and then combined to produce the full length molecule.

THERAPEUTICS

Chemical and structural homology exists between VTRP and the vesicle transport related protein from mouse, ANK1 (GI 1658116). In addition, VTRP is expressed in cancerous tissues and immortalized cell lines. Therefore, VTRP appears to play a role in cancer and immune disorders.

Therefore, in one embodiment, an antagonist of VTRP may be administered to a subject to treat or prevent a cancer. Cancers may include, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds VTRP may be used directly as an antagonist or indirectly as a targeting or delivery mechanism for bringing a pharmaceutical agent to cells or tissue which express VTRP.

In another embodiment, a vector expressing the complement of the polynucleotide encoding VTRP may be administered to a subject to treat or prevent a cancer including, but not limited to, those described above.

In another embodiment, an antagonist of VTRP may be administered to a subject to treat or prevent an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections, and trauma.

In another embodiment, a vector expressing the complement of the polynucleotide encoding VTRP may be administered to a subject to treat or prevent an immune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of VTRP may be produced using methods which are generally known in the art. In particular, purified VTRP may be used to produce antibodies or to screen libraries of pharmaceutical agents to identify those which specifically bind VTRP. Antibodies to VTRP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with VTRP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to VTRP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of VTRP amino acids may be fused with those of another protein, such as KLH, and antibodies to the chimeric molecule may be produced.

Monoclonal antibodies to VTRP may be prepared using any technique which provides for the production of antibody molecules by continuous cell lines in culture. These include, but are not limited to, the hybridoma technique, the human B-cell hybridoma technique, and the EBV-hybridoma technique. (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce VTRP-specific single chain antibodies. Antibodies with related specificity, but of distinct idiotypic composition, may be generated by chain shuffling from random combinatorial immunoglobulin libraries. (Burton D. R. (1991) Proc. Natl. Acad. Sci. 88:11120–11123.)

Antibodies may also be produced by inducing in vivo production in the lymphocyte population or by screening immunoglobulin libraries or panels of highly specific binding reagents as disclosed in the literature. (Orlandi, R. et al. (1989) Proc. Natl. Acad. Sci. 86: 3833–3837, and Winter, G. et al. (1991) Nature 349:293–299.) Antibody fragments which contain specific binding sites for VTRP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (Huse, W. D. et al. (1989) Science 254:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between VTRP and its specific antibody. A two-site, monoclonal-based immunoassay utilizing monoclonal antibodies reactive to two non-interfering VTRP epitopes is preferred, but a competitive binding assay may also be employed. (Maddox, supra.)

In another embodiment of the invention, the polynucleotides encoding VTRP, or any fragment or complement thereof, may be used for therapeutic purposes. In one aspect, the complement of the polynucleotide encoding VTRP may be used in situations in which it would be desirable to block the transcription of the mRNA. In particular, cells may be transformed with sequences complementary to polynucleotides encoding VTRP. Thus, complementary molecules or fragments may be used to modulate VTRP activity, or to achieve regulation of gene function. Such technology is now well known in the art, and sense or antisense oligonucleotides or larger fragments can be designed from various locations along the coding or control regions of sequences encoding VTRP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those Askilled in the art can be used to construct vectors which will express nucleic acid sequence complementary to the polynucleotides of the gene encoding VTRP. These techniques are described, for example, in Sambrook (supra) and in Ausubel (supra).

Genes encoding VTRP can be turned off by transforming a cell or tissue with expression vectors which express high levels of a polynucleotide or fragment thereof encoding VTRP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding VTRP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (Gee, J. E. et al. (1994) in Huber, B. E. and B. I. Carr, *Molecular and Immunologic Approaches*, Futura Publishing Co., Mt. Kisco, N.Y.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules specifically and efficiently catalyze endonucleolytic cleavage of sequences encoding VTRP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding VTRP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art, such as those described in Goldman, C. K. et al. (1997; Nature Biotechnology 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of VTRP, antibodies to VTRP, and mimetics, agonists, antagonists, or inhibitors of VTRP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of VTRP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays of neoplastic cells, for example, or in animal models, usually mice, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example VTRP or fragments thereof, antibodies of VTRP, and agonists, antagonists or inhibitors of VTRP, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio between therapeutic and toxic effects is the therapeutic index, and it can be expressed as the LD50/ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on the half-life and clearance rate of the particular formulation.

Normal dosage amounts may vary from 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind VTRP may be used for the diagnosis of disorders characterized by expression of VTRP, or in assays to monitor patients being treated with VTRP or agonists, antagonists, and inhibitors of VTRP. Antibodies useful for diagnostic purposes may be prepared in the same manner as those described above for therapeutics. Diagnostic assays for VTRP include methods which utilize the antibody and a label to detect VTRP in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring VTRP, including ELISAs, RIAs, and FACS, are known in the art and provide a basis for diagnosing altered or abnormal levels of VTRP expression. Normal or standard values for VTRP expression are established by combining body fluids or cell extracts taken from normal mammalian subjects, preferably human, with is antibody to VTRP under conditions suitable for complex formation The amount of standard complex formation may be quantified by various methods, preferably by photometric means. Quantities of VTRP expressed in subject, control, and disease samples from biopsied tissues are compared with the standard values. Deviation between standard and subject values establishes the parameters for diagnosing disease.

In another embodiment of the invention, the polynucleotides encoding VTRP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of VTRP may be correlated with disease. The diagnostic assay may be used to distinguish between absence, presence, and excess expression of VTRP, and to monitor regulation of VTRP levels during therapeutic intervention.

In one aspect, hybridization with PCR probes which are capable of detecting polynucleotide sequences, including genomic sequences, encoding VTRP or closely related molecules may be used to identify nucleic acid sequences which encode VTRP. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding VTRP, alleles, or related sequences.

Probes may also be used for the detection of related sequences, and should preferably contain at least 50% of the nucleotides from any of the VTRP encoding sequences. The hybridization probes of the subject invention may be DNA or RNA and may be derived from the sequence of SEQ ID NO:2 or SEQ ID NO:4 or from genomic sequences including promoter and enhancer elements and introns of the naturally occurring VTRP.

Means for producing specific hybridization probes for DNAs encoding VTRP include the cloning of polynucleotide sequences encoding VTRP or VTRP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding VTRP may be used for the diagnosis of a disorder associated with expression of VTRP. Examples of such a disorder include cancer, such as adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, flngal, parasitic, protozoal, and helminthic infections, and trauma. The polynucleotide sequences encoding VTRP may be used in Southern or northern analysis, dot blot, or other membrane-based technologies; in PCR technologies; in dipstick, pin, and ELISA assays; and in microarrays utilizing fluids or tissues from patient biopsies to detect altered VTRP expression. Such qualitative or quantitative methods are well known in the art.

In a particular aspect, the nucleotide sequences encoding VTRP may be useful in assays that detect the presence of associated disorders, particularly those mentioned above. The nucleotide sequences encoding VTRP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding VTRP in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of VTRP, a normal or standard profile for expression is established. This may be accomplished by combining body fluids or cell extracts taken from normal subjects, either animal or human, with a sequence, or a fragment thereof, encoding VTRP, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding VTRP may involve the use of PCR. Such oligomers may be chemically synthesized, generated enzymatically, or produced in vitro. Oligomers will preferably consist of two nucleotide sequences, one with sense orientation (5' to 3') and another with antisense orientation (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of VTRP include radiolabeling or biotinylating nucleotides, coamplification of a control nucleic acid, and interpolating results from standard curves. (Melby, P. C. et al. (1993) J. Immunol. Methods 159:235–244, and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In ftrther embodiments, oligonucleotides or longer fragments derived from any of the polynucleotide sequences described herein may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

In one embodiment, the microarray is prepared and used according to methods known in the art, such as those described in published PCT application WO95/11995 (Chee et al.), Lockhart, D. J. et al. (1996; Nat. Biotech. 14:1675–1680), and Schena, M. et al. (1996; Proc. Natl. Acad. Sci. 93:10614–10619).

The microarray is preferably composed of a large number of unique single-stranded nucleic acid sequences, usually either synthetic antisense oligonucleotides or fragments of cDNAs, fixed to a solid support. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides which are about 7 to 10 nucleotides in length. The microarray may contain oligonucleotides which cover the known 5' or 3' sequence, or may contain sequential oligonucleotides which cover the full length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable solid support.

In one aspect, the oligonucleotides may be synthesized on the surface of the substrate by using a chemical coupling procedure and an ink jet application apparatus, such as that described in published PCT application WO95/251116 (Baldeschweiler et al.). In another aspect, a grid array analogous to a dot or slot blot (HYBRIDOT® apparatus, GIBCO/BRL) may be used to arrange and link cDNA fragments or oligonucleotides to the surface of a substrate using a vacuum system or thermal, UV, mechanical or chemical bonding procedures. In yet another aspect, an array may be produced by hand or by using available devices, materials, and machines (including Brinkmann® multichannel pipettors or robotic instruments), and may contain 8, 24, 96, 384, 1536, or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and OLIGOLABELING or TRANSPROBE kits (Pharmacia & Upjohn) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine the degree of complementarity and the relative abundance of each oligonucleotide sequence on the microarray. A detection system may be used to measure the absence, presence, and amount of hybridization for all of the distinct sequences simultaneously. This data may be used for large scale correlation studies or for functional analysis of the sequences, mutations, variants, or polymorphisms among samples. (Heller, R. A. et al. (1997) Proc. Natl. Acad. Sci. 94:2150–2155.)

In another embodiment of the invention, nucleic acid sequences encoding VTRP may be used to generate hybridization probes useful for mapping the naturally occurring genomic sequence. The sequences may be mapped to a particular chromosome, to a specific region of a chromosome, or to artificial chromosome constructions, such as human artificial chromosomes (HACs), yeast artificial chromosomes (YACs), bacterial artificial chromosomes (BACs), bacterial PI constructions, or single chromosome cDNA libraries, such as those reviewed in Price, C. M. (1993; Blood Rev. 7:127–134) and Trask, B. J. (1991; Trends Genet. 7:149–154).

Fluorescent in situ hybridization (FISH, as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at the Online Mendelian Inheritance in Man (OMIM) site. Correlation between the location of the gene encoding VTRP on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

In another embodiment of the invention, VTRP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between VTRP and the agent being tested may be measured.

Another technique for drug screening which may be used provides for high throughput screening of compounds having suitable binding affinity to the protein of interest as described in published PCT application WO84/03564. In this method, large numbers of different small test compounds are synthesized on a solid substrate, such as plastic pins or some other surface. The test compounds are reacted with VTRP, or fragments thereof, and washed. Bound VTRP is then detected by methods well known in the art. Purified VTRP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding VTRP specifically compete with a test compound for binding VTRP. In this manner, antibodies can be used to detect the presence of any peptide which shares one or more antigenic determinants with VTRP.

In additional embodiments, the nucleotide sequences which encode VTRP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. MUSCNOT01 cDNA Library Construction

The MUSCNOT01 library was custom-constructed by Stratagene from skeletal muscle tissue obtained from a 47 year old male. The frozen tissue was ground by mortar and pestle and lysed in buffer containing guanidium isothiocynate. RNA was extracted several times with phenol-chloroform and precipitated with ethanol. Poly(A+)RNA was isolated using biotinylated oligo d(T) primer and streptavidin coupled to a paramagnetic particle (Promega Corp., Madison, Wis.). The cDNA library was prepared using oligo d(T) priming. Synthetic adaptor oligonucleotides were ligated onto cDNA ends enabling insertion into UNI-ZAP vector system (Stratagene).

The cDNA library was screened using DNA probes, and the BLUESCRIPT phagemid (Stratagene) was excised. The custom-constructed library phage particles were transfected into *E. coli* host strain XL1-BlUE competent cells (Stratagene). Alternative unidirectional vectors include, but are not limited to, pcDNAI (Invitrogen, San Diego, Calif.) and PSHLOX-1 (Novagen, Madison, Wis.).

II. Isolation and Sequencing of cDNA Clones

The phagemid forms of individual cDNA clones were obtained by the in vivo excision process, in which the host bacterial strain was coinfected with both the lambda library phage and an f1 helper phage. Polypeptides derived from both the library-containing phage and the helper phage nicked the lambda DNA, initiated new DNA synthesis from defined sequences on the lambda target DNA and created a smaller, single stranded circular phagemid DNA molecule that included all DNA sequences of the pBluescripto® plasmid and the cDNA insert.

The phagemid DNA was secreted from the cells, purified, and used to re-infect fresh host cells, where the double stranded phagemid DNA was produced. Because the phagemid carries the gene for β-lactamase, the newly-transformed bacteria are selected on medium containing ampicillin.

Phagemid DNA was also purified using the QIAWELL-8 plasmid, QIAWELL PLUS, and QIAWELL ULTRA DNA purification system (QIAGEN, Chatsworth, Calif.). The DNA was eluted from the purification resin and prepared for DNA sequencing and other analytical manipulations.

The cDNA inserts from random isolates were sequenced in part. Conventional enzymatic methods employ DNA polymerase Klenow fragment, SEQUENASE DNA polymerase or Taq polymerase to extend DNA chains from an oligonucleotide primer annealed to the DNA template of interest. Methods have been developed for the use of both single- and double stranded templates. The chain termination reaction products are usually electrophoresed on urea-acrylamide gels and are detected either by autoradiography (for radionuclide-labeled precursors) or by fluorescence (for fluorescent-labelled precursors). Recent improvements in mechanized reaction preparation, sequencing and analysis using the fluorescent detection method have permitted expansion in the number of sequences that can be determined per day (such as the Applied Biosystems 373 DNA sequencer and CATALYST 800).

III. Homology Searching of cDNA Clones and Their Deduced Proteins

Each cDNA was compared to sequences in GenBank using a search algorithm developed by Applied Biosystems and incorporated into the INHERIT-670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT- 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (Sambrook, supra).

Analogous computer techniques applying BLAST are used to search for identical or related molecules in nucleotide databases such as GenBank or the LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

% sequence identity×% maximum BLAST score/100

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding VTRP occurs. Abundance and percent abundance are also reported. Abundance directly reflects the number of times a particular transcript is represented in a cDNA library, and percent abundance is abundance divided by the total number of sequences examined in the cDNA library.

V. Extension of VTRP Encoding Polynucleotides

The nucleic acid sequence of Incyte Clone 118064 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new unknown nucleotide sequence for the region of interest. The initial primers were designed from the cDNA using OLIGO 4.06 primer analysis sortware (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier thermal cycler (PTC200; M. J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 $\mu$l to 10 $\mu$l aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using the QIAQUICK DNA purification kit (QIAGEN Inc., Chatsworth, Calif.), and trimmed of overhangs using Klenow enzyme to facilitate religation and cloning.

After ethanol precipitation, the products were redissolved in 13 $\mu$l of ligation buffer, 1 $\mu$l T4-DNA ligase (15 units) and 1 $\mu$l T4 polynucleotide kinase were added, and the mixture was incubated at room temperature for 2 to 3 hours, or overnight at 16° C. Competent *E. coli* cells (in 40 $\mu$l of appropriate media) were transformed with 3 $\mu$l of ligation mixture and cultured in 80 $\mu$l of SOC medium. (Sambrook, supra). After incubation for one hour at 37° C., the *E. coli* mixture was plated on Luria Bertani (LB) agar (Sambrook, supra) containing 2× Carb. The following day, several colonies were randomly picked from each plate and cultured in 150 $\mu$l of liquid LB/2× Carb medium placed in an individual well of an appropriate commercially-available sterile 96-well microtiter plate. The following day, 5 $\mu$l of each overnight culture was transferred into a non-sterile 96-well plate and, after dilution 1:10 with water, 5 $\mu$l from each sample was transferred into a PCR array.

For PCR amplification, 18 $\mu$l of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 primer analysis software (National Biosciences) and labeled by combining 50 pmol of each oligomer and 250 $\mu$Ci of [$\gamma$-$^{32}$P] adenosine triphosphate (Amersham) and T4 polynucleotide kinase (DuPont NEN®, Boston, Mass.). The labeled oligonucleotides are substantially purified using a SEPHADEX G-25 superfine resin colurnn (Pharmacia & Upjohn). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN®).

The DNA from each digest is fractionated on a 0.7 percent agarose gel and transferred to nylon membranes (NYTRAN PLUS, Schleicher & Schuell, Durham, NH). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR autoradiography film (Kodak, Rochester, N.Y.) is exposed to the blots, or the blots are placed PHOSPHOIMAGER in a PHOSPHOIMAGER cassette (Molecular Dynamics, Sunnyvale, Calif.) for several hours, hybridization patterns are compared visually.

VII. Microarrays

To produce oligonucleotides for a microarray, one of the nucleotide sequences of the present invention is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20-mers are synthesized and arranged on the surface of the silicon chip using a light-directed chemical process, such as that described in Chee (supra).

In the alternative, a chemical coupling procedure and an ink jet device are used to synthesize oligomers on the surface of a substrate. (See Baldeschweiler, supra.) In another alternative, a grid array analogous to a dot or slot blot is used to arrange and link cDNA fragments or oligonucleotides to the surface of a substrate using a vacuum system or thermal, UV, mechanical, or chemical bonding procedures. A typical array may be produced by hand or using available materials and machines and contain grids of 8 dots, 24 dots, 96 dots, 384 dots, 1536 dots, or 6144 dots. After hybridization, the microarray is washed to remove nonhybridized probes, and a scanner is used to determine the levels and patterns of fluorescence. The scanned image is examined to determine the degree of complementarity and the relative abundance/expression level of each oligonucleotide sequence in the microarray.

VIII. Complementary Polynucleotides

Sequence complementary to the VTRP-encoding sequence, or any part thereof, is used to detect, decrease, or inhibit expression of naturally occurring VTRP. Although use of oligonucleotides comprising from about 15 to 30 base pairs is described, essentially the same procedure is used with smaller or with larger sequence fragments. Appropriate oligonucleotides are designed using OLIGO 4.06 primer analysis software and the coding sequence of VTRP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the VTRP-encoding transcript.

IX. Expression of VTRP

Expression of VTRP is accomplished by subcloning the cDNAs into appropriate vectors and transforming the vectors into host cells. In this case, the cloning vector is also used to express VTRP in *E. coli*. This vector contains a promoter for β-galactosidase upstream of the cloning site, followed by sequence containing the amino-terminal Met and the subsequent seven residues of β-galactosidase. Immediately following these eight residues is a bacteriophage promoter useful for transcription and a linker containing a number of unique restriction sites.

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of VTRP into bacterial growth media which can be used directly in the following assay for activity. in the following assay for activity.

X. Demonstration of VTRP Activity

VTRP activity can be measured on the basis of the known function of ANK1 (GI 1658116), derived from the C-terminal domain of erythrocyte ankyrin, as a modifier of the spectrin-binding activity of ankyrin. In particular, cleavage of the ANK1 region from mouse erythrocyte ankyrin by calpain reduces spectrin-binding activity of the remaining 195 kDa fragment~8-fold (Hall, T. G. and V. Bennett (1987) J. Biol. Chem. 262:10537–45). VTRP activity is therefore measured by comparing the spectrin-binding activity of the 195 kDa calpain fragment with a chimeric recombinant protein containing VTRP integrated with the 195 kDa calpain fragment. Spectrin binding is measured by incubating the VTRP recombinant protein or 195 kDa fragment with radiolabeled-$^{14}C$-spectrin together in a suitable buffer. Following the reaction, $^{14}C$-spectrin and protein-bound $^{14}C$-spectrin are separated by gel electrophoresis, and the latter spot cut out and counted in a radioisotope counter. The ratio of the radioactivity recovered in association with VTRP recombinant protein compared to that found in association with the 195 kDa fragment is proportional to the activity of VTRP in the assay.

XI. Production of VTRP Specific Antibodies

VTRP substantially purified using PAGE electrophoresis (Sambrook, supra), or other purification techniques, is used to immunize rabbits and to produce antibodies using standard protocols. The VTRP amino acid sequence is analyzed using DNASTAR software (DNASTAR Inc) to determine regions of high immunogenicity, and a corresponding oligopeptide is synthesized and used to raise antibodies by means known to those of skill in the art. Selection of appropriate epitopes, such as those near the C-terminus or in hydrophilic regions, is described by Ausubel (supra) and by others.

Typically, the oligopeptides are 15 residues in length, and are synthesized using an Applied Biosystems 431A peptide synthesizer using fmoc-chemistry and coupled to KLH (Sigma, St. Louis, Mo.) by reaction with N-maleimidobenzoyl-N-hydroxysuccinimide ester (MBS), following the procedure described in Ausubel et al., supra. Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring VTRP Using Specific Antibodies

Naturally occurring or recombinant VTRP is substantially purified by immunoaffinity chromatography using antibodies specific for VTRP. An immunoaffinity column is constructed by covalently coupling VTRP antibody to an activated chromatographic resin, such as CNBr-activated SEPHAROSE (Pharmacia & Upjohn). After the coupling, the resin is blocked and washed according to the manufacturer's instructions.

Media containing VTRP are passed over the immunoaffinity column, and the column is washed under conditions that allow the preferential absorbance of VTRP (e.g., high ionic strength buffers in the presence of detergent). The column is eluted under conditions that disrupt antibodyN-TRP binding (e.g., a buffer of pH 2 to pH 3, or a high concentration of a chaotrope, such as urea or thiocyanate ion), and VTRP is collected.

XIII. Identification of Molecules Which Interact with VTRP

VTRP or biologically active fragments thereof are labeled with $^{125}I$ Bolton-Hunter reagent. (Bolton et al. (1973) Biochem. J. 133:529.) Candidate molecules previously arrayed in the wells of a multi-well plate are incubated with the labeled VTRP, washed, and any wells with labeled VTRP complex are assayed. Data obtained using different concentrations of VTRP are used to calculate values for the number, affinity, and association of VTRP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. A composition comprising the polynucleotide sequence of claim 1.

3. An isolated and purified polynucleotide sequence which is fully complementary to the polynucleotide sequence of claim 1.

4. An isolated and purified polynucleotide sequence comprising SEQ ID NO:2.

5. An isolated and purified polynucleotide sequence which is fully complementary to the polynucleotide sequence of claim 4.

6. An expression vector comprising the polynucleotide sequence of claim 1.

7. A host cell comprising the expression vector of claim 6.

8. A method for producing a polypeptide comprising the amino acid sequence of SEQ ID NO:1, the method comprising the steps of:

(a) culturing the host cell of claim 7 under conditions suitable for the expression of the polypeptide; and (b) recovering the polypeptide from the host cell culture.

9. A method for detecting a polynucleotide in a biological sample containing nucleic acids, the method comprising the steps of:

(a) hybridizing the polynucleotide of claim 3 to at least one of the nucleic acids of the biological sample, thereby forming a hybridization complex; and (b) detecting the hybridization complex.

10. The method of claim 9 wherein the nucleic acids of the biological sample are amplified by the polymerase chain reaction prior to the hybridizing step.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
(A) LENGTH: 214 amino acids
(B) TYPE: amino acid
(C) STRANDEDNESS: single
(D) TOPOLOGY: linear (vii) IMMEDIATE SOURCE:
(A) LIBRARY: MUSCNOT01
(B) CLONE: 118064

(xi) SEQUENCE DESCRIPTION: SEQ ID NO:1:

```
Met Trp Thr Phe Val Thr Gln Leu Leu Val Thr Leu Val Leu Leu Ser
 1               5                  10                  15

Phe Phe Leu Val Ser Cys Gln Asn Val Met His Ile Val Arg Gly Ser
            20                  25                  30

Leu Cys Phe Val Leu Lys His Ile His Gln Glu Leu Asp Lys Glu Leu
        35                  40                  45

Gly Glu Ser Glu Gly Leu Ser Asp Asp Glu Glu Thr Ile Ser Thr Arg
    50                  55                  60

Val Val Arg Arg Arg Val Phe Leu Lys Gly Asn Glu Phe Gln Asn Ile
65                  70                  75                  80

Pro Gly Glu Gln Val Thr Glu Glu Gln Phe Thr Asp Glu Gln Gly Asn
                85                  90                  95

Ile Val Thr Lys Lys Ile Ile Arg Lys Val Val Arg Gln Ile Asp Leu
            100                 105                 110

Ser Ser Ala Asp Ala Ala Gln Glu His Glu Glu Val Glu Leu Arg Gly
        115                 120                 125

Ser Ala Leu Gln Pro Asp Leu Ile Glu Ala Arg Lys Gly Ala Gln Ile
    130                 135                 140

Leu Lys Arg Ala Ser Leu Lys Lys Gly Glu Thr Val Thr Pro Ser Arg
145                 150                 155                 160

Ser Pro Trp Ser Ser Leu Ser Gly Gly Ser His Leu Asp Thr Gln Pro
                165                 170                 175

Leu Asn Pro Thr His Ser Ala Met His Thr Gly Gly Glu Leu Asp Leu
            180                 185                 190

Arg Ala Thr Ala Ala Val His Thr Phe Leu Trp Ala Asp Gly Met Thr
        195                 200                 205

Ser Val Arg Asp Ser Cys
    210
```

(2) INFORMATION FOR SEQ ID NO:2:

(i) SEQUENCE CHARACTERISTICS:
(A) LENGTH: 1156 base pairs
(B) TYPE: nucleic acid
(C) STRANDEDNESS: single
(D) TOPOLOGY: linear (vii) IMMEDIATE SOURCE:
(A) LIBRARY: MUSCNOT01
(B) CLONE: 118064

(xi) SEQUENCE DESCRIPTION: SEQ ID NO:2:

```
GCCGAGAGGG CCATTCGGTG TCCTGCCCAC AGAGAGAGAA ACAGTGAGAG ACCAAGAGAG      60
```

```
CAAACCAGAG AGATACGGAG GGGGAATGCA AGGGGTCCCT GGGGGACTCA GGAGTCCCAG    120

TGGAGAATGA GAGGCAGGCC CCCCGTGGTG GCCGGGGCCC TGGCTGCCAG AGGACCGGGC    180

TGGTGAGGAG GCGAGGATGT GGACTTTCGT CACCCAGCTG TTGGTCACGC TGGTGCTGCT    240

GAGCTTCTTC CTGGTCAGCT GTCAGAACGT GATGCACATT GTCAGGGGGT CCCTGTGCTT    300

TGTGCTAAAG CACATCCACC AGGAGCTGGA CAAGGAGCTG GGGGAGAGCG AGGGCCTCAG    360

TGACGACGAG GAGACCATCT CCACCAGGGT GGTCCGGCGG CGGGTCTTCC TGAAGGGGAA    420

TGAGTTTCAG AATATTCCAG GGGAGCAGGT GACAGAGGAG CAATTCACGG ATGAGCAGGG    480

CAACATTGTC ACCAAGAAGA TCATTCGCAA GGTGGTTCGA CAGATAGACT TGTCCAGCGC    540

CGATGCCGCC CAGGAGCACG AGGAGGTGGA GCTGAGAGGG AGTGCCCTAC AGCCGGACCT    600

GATAGAGGCC AGGAAGGGGG CGCAGATATT GAAGCGGGCC AGCCTGAAAA AGGGGGAAAC    660

AGTGACCCCG AGCCGCTCTC CTTGGAGTAG CCTCTCGGGA GGATCACACC TCGACACCCA    720

ACCCCTGAAC CCCACACACT CTGCCATGCA CACAGGAGGA GAGCTGGACC TGAGGGCCAC    780

CGCAGCGGTG CACACATTCC TCTGGGCTGA CGGCATGACC TCTGTAAGGG ACTCCTGCTA    840

GTCCCCTCTT GGCATGAATG ACTGACTGTA GACGCATGAC CTCCAGGCTT CAATCCTGCC    900

TCTTGCAATG ACAGCTGATC TGTCGGAACC AGGACACAAA AGCAGCAAGA AGCGGGGAGA    960

GAGAGGGATA GAAAACAAGC GCAGGAGAGC CTGCGAACGC AAAAGTGAAT GAGGGCTTTT   1020

TGTGGCTGGG GATGGGTTTT GGTTTTGGGG TTTTTTTTTT TTAAATTGTT TTGACTCCGT   1080

ACAGGGTACT TTTCCCTAAC CTCATCTGTC AGAAATCCAT GTGGCCTTCC TGGAAAGAAA   1140

AAAAAAAAAA AAAAAA                                                   1156
```

(2) INFORMATION FOR SEQ ID NO:3:

(i) SEQUENCE CHARACTERISTICS:
(A) LENGTH: 155 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 1658116

(xi) SEQUENCE DESCRIPTION: SEQ ID NO:3:

```
Met Trp Thr Phe Ile Thr Gln Leu Leu Val Thr Leu Val Leu Leu Gly
 1               5                  10                  15

Phe Phe Leu Val Ser Cys Gln Asn Val Met His Ile Val Lys Gly Ser
            20                  25                  30

Leu Cys Phe Val Leu Lys His Ile His Gln Glu Leu Asp Lys Glu Leu
        35                  40                  45

Gly Glu Ser Glu Gly Leu Ser Asp Asp Glu Glu Thr Ile Ser Thr Arg
    50                  55                  60

Val Val Arg Arg Arg Val Phe Leu Lys Gly Asp Glu Leu Gln Asn Ile
65                  70                  75                  80

Pro Gly Glu Gln Val Thr Glu Glu Gln Phe Thr Asp Glu Gln Gly Asn
                85                  90                  95

Ile Val Thr Lys Lys Ile Ile Arg Lys Val Val Arg Gln Val Asp Ser
            100                 105                 110

Ser Gly Ala Ile Asp Thr Gln Gln His Glu Glu Val Glu Leu Arg Gly
        115                 120                 125

Ser Gly Leu Gln Pro Asp Leu Ile Glu Gly Arg Lys Gly Ala Gln Ile
    130                 135                 140
```

-continued

```
Val Lys Arg Ala Ser Leu Lys Arg Gly Lys Gln
145                 150                 155
```